United States Patent
Presby

(10) Patent No.: US 8,807,345 B2
(45) Date of Patent: Aug. 19, 2014

(54) APPARATUS AND METHOD FOR ANALYZING AGGREGATE

(75) Inventor: David W. Presby, Sugar Hill, NH (US)

(73) Assignee: Presby Patent Trust, Whitefield, NH (US)

( * ) Notice: Subject to any disclaimer, the term of this patent is extended or adjusted under 35 U.S.C. 154(b) by 0 days.

(21) Appl. No.: 13/367,968

(22) Filed: Feb. 7, 2012

(65) Prior Publication Data

US 2013/0032512 A1 Feb. 7, 2013

Related U.S. Application Data

(60) Provisional application No. 61/440,098, filed on Feb. 7, 2011.

(51) Int. Cl.
| | |
|---|---|
| *B07B 1/22* | (2006.01) |
| *B07B 1/18* | (2006.01) |
| *G01N 33/38* | (2006.01) |
| *G01N 15/00* | (2006.01) |
| *G01N 15/02* | (2006.01) |

(52) U.S. Cl.
CPC .......... *B07B 1/18* (2013.01); *G01N 2015/0096* (2013.01); *G01N 33/38* (2013.01); *G01N 2015/0092* (2013.01); *G01N 15/0272* (2013.01)
USPC ............... 209/291; 209/13; 209/17; 209/268; 209/290; 210/335; 210/337; 210/338; 210/499; 210/497.01; 210/497.3

(58) Field of Classification Search
USPC ........... 209/274, 289–291, 300, 370, 372, 13, 209/17, 268; 210/335, 337, 338, 499, 210/497.01, 497.3
See application file for complete search history.

(56) References Cited

U.S. PATENT DOCUMENTS

| | | | | | |
|---|---|---|---|---|---|
| 29,069 | A | * | 7/1860 | Fitch | 210/335 |
| 1,430,664 | A | * | 10/1922 | Madson | 209/291 |
| 1,554,976 | A | * | 9/1925 | Kearns | 209/291 |
| 2,264,223 | A | * | 11/1941 | Stancliffe | 209/237 |
| 2,442,818 | A | * | 6/1948 | Lyman | 210/237 |
| 2,587,272 | A | * | 2/1952 | Anderson | 209/291 |
| 2,601,924 | A | * | 7/1952 | Gonder | 209/284 |
| 3,768,557 | A | | 10/1973 | Spurlock et al. | |
| 5,215,661 | A | | 6/1993 | Tanabe | |
| 5,429,248 | A | * | 7/1995 | Le Gigan et al. | 209/33 |
| 5,565,097 | A | * | 10/1996 | Hayday | 210/167.31 |
| 5,954,451 | A | | 9/1999 | Presby | |
| 5,972,211 | A | * | 10/1999 | Jones | 210/90 |
| 2004/0060858 | A1 | | 4/2004 | Lucas et al. | |
| 2006/0027492 | A1 | * | 2/2006 | Lin | 210/338 |
| 2007/0090040 | A1 | * | 4/2007 | Bauder et al. | 210/338 |
| 2007/0256834 | A1 | | 11/2007 | Hopkins et al. | |
| 2008/0308484 | A1 | * | 12/2008 | Deb et al. | 210/257.1 |
| 2011/0168606 | A1 | * | 7/2011 | Bingham | 209/135 |

FOREIGN PATENT DOCUMENTS

WO 2012109230 8/2012

* cited by examiner

*Primary Examiner* — Prasad Gokhale
(74) *Attorney, Agent, or Firm* — Finch & Maloney PLLC

(57) ABSTRACT

A device, method, and system for analyzing aggregate are described. An exemplary device may include a housing with one or more grading screens. Aggregate and liquid may be received by a port within the housing. The liquid and any suspended fines, after passing through the one or more grading screens and aggregate, may be received into an observation container for observing the clarity of the liquid.

21 Claims, 13 Drawing Sheets

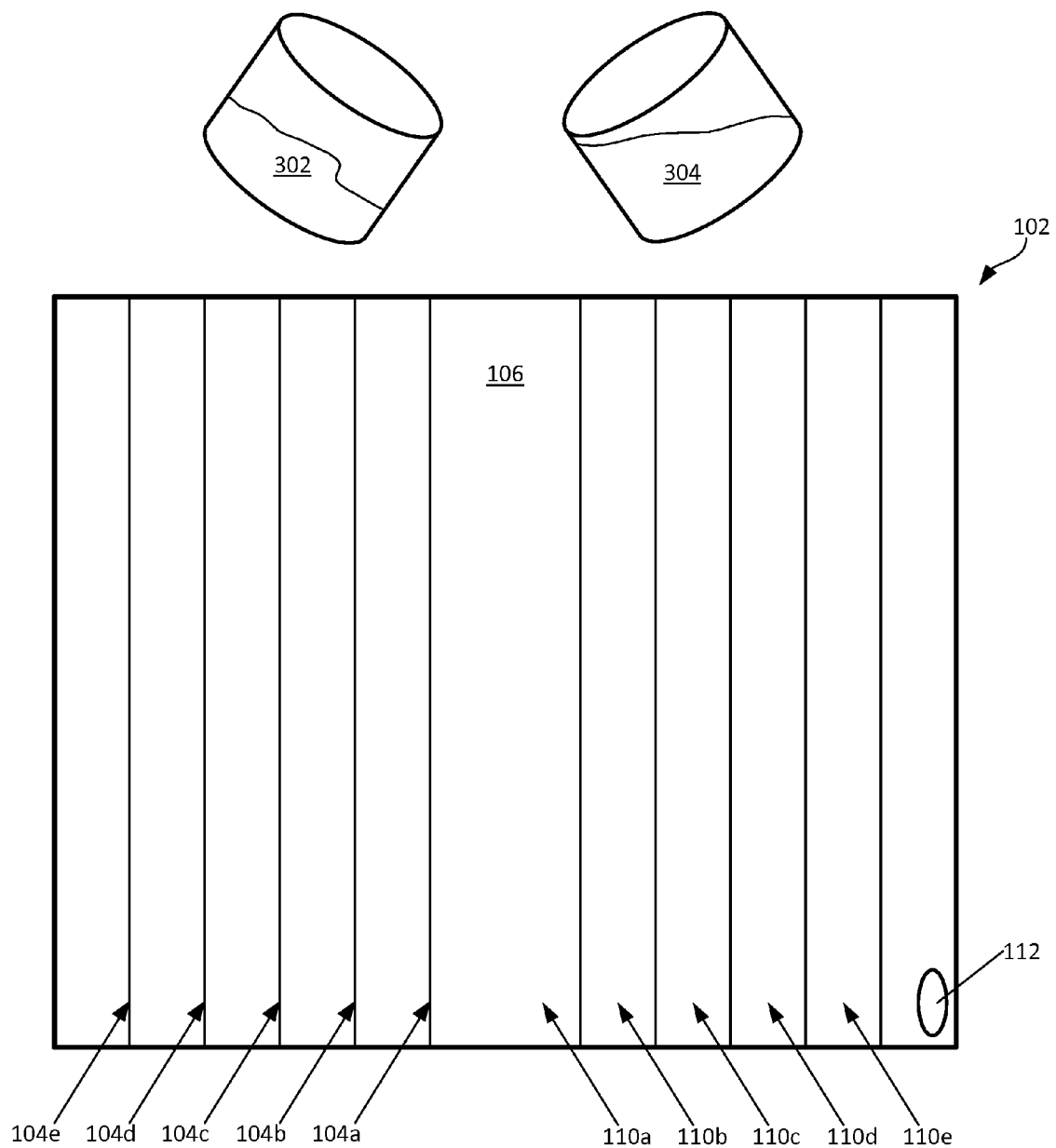

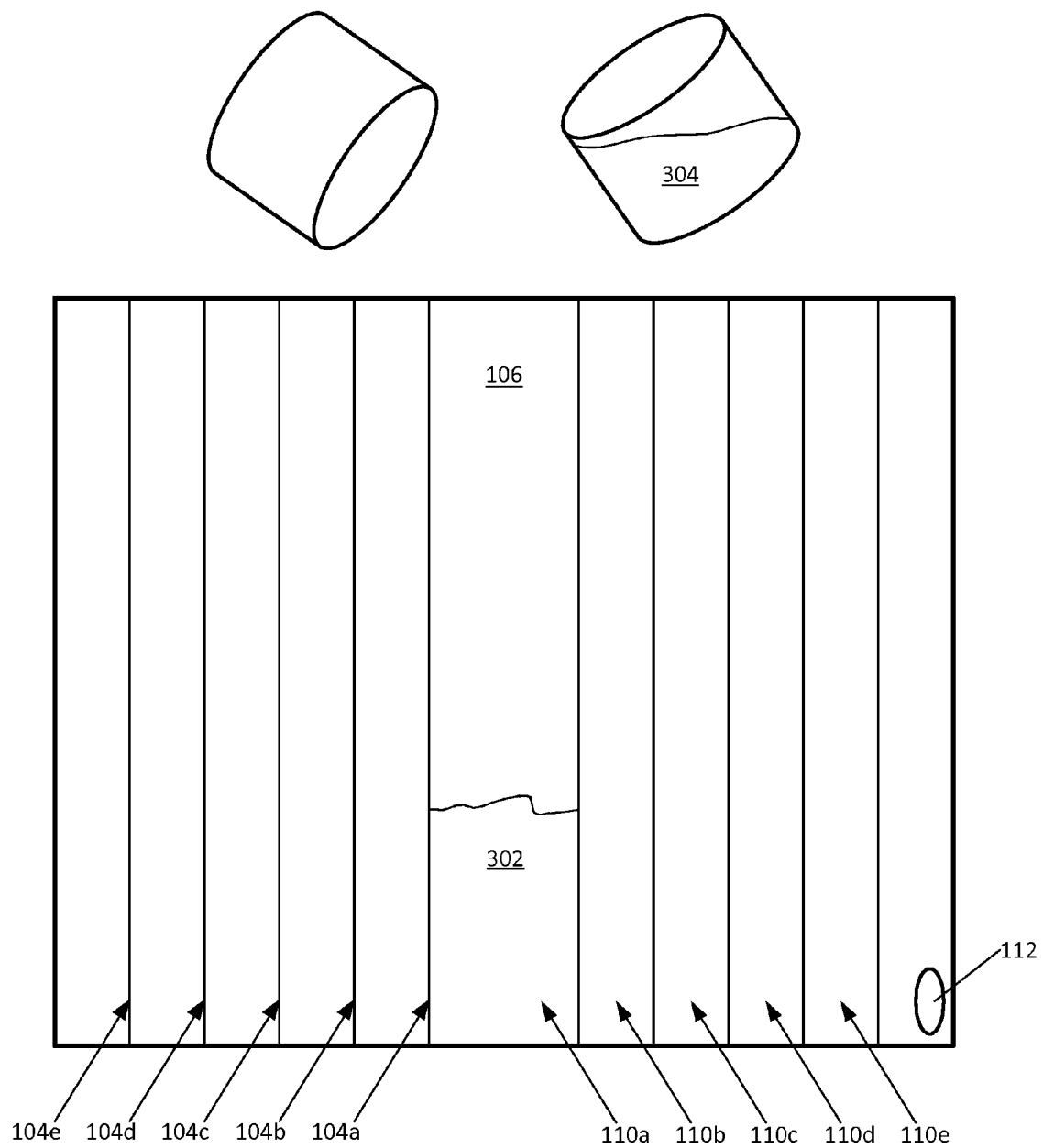

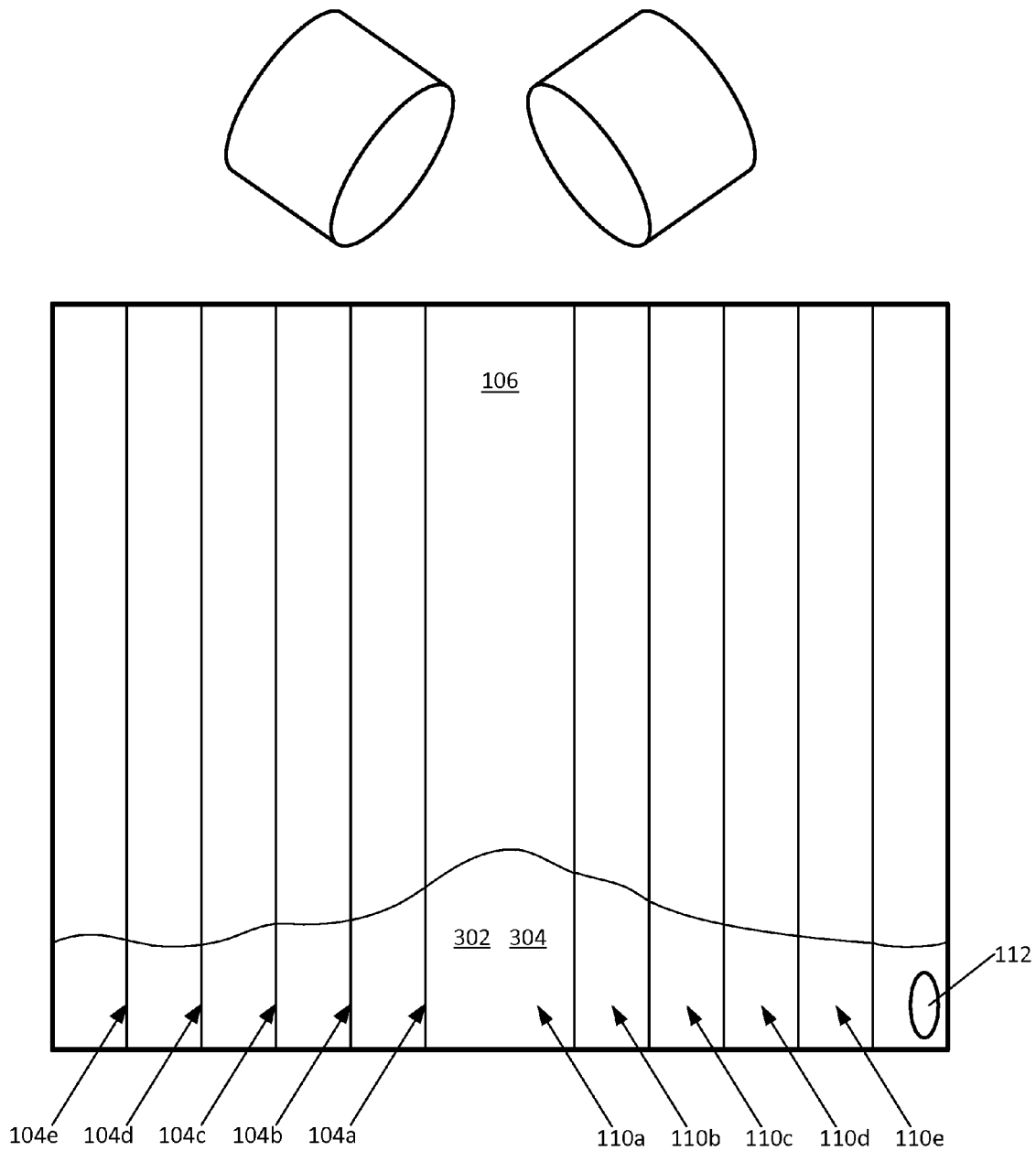

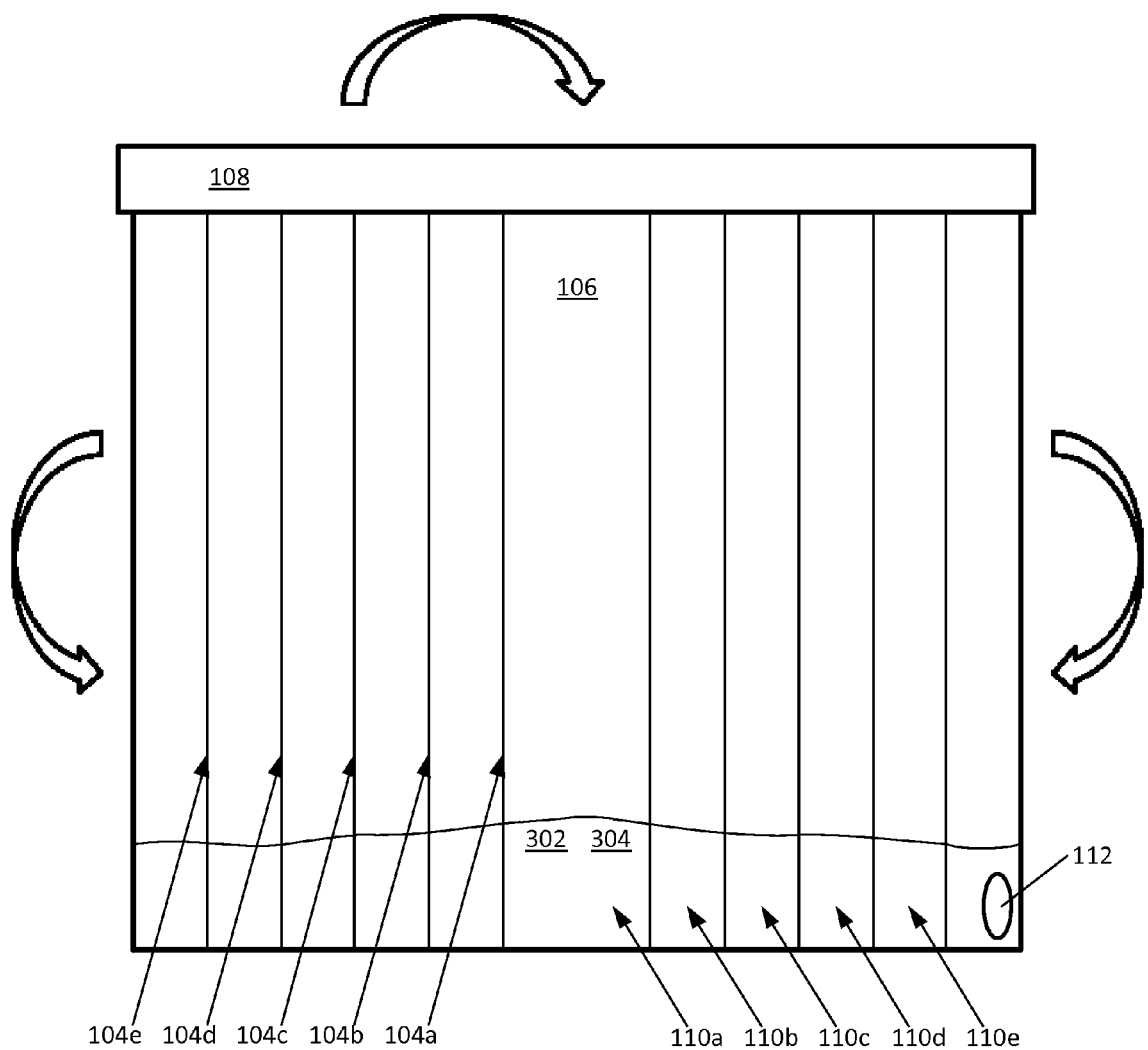

APPARATUS AND METHOD FOR ANALYZING AGGREGATE

CROSS-REFERENCE TO RELATED APPLICATIONS

This application claims benefit of U.S. Provisional Patent Application Ser. No. 61/440,098, filed on Feb. 7, 2011. Each patent and patent application cited herein is hereby incorporated by reference in its entirety.

BACKGROUND

1. Field of the Invention

The invention relates to analyzing aggregate and, in particular, to identifying composition of granularity of aggregate.

2. Discussion of Related Art

Many concrete products define the requirements for grading and quality of fine and coarse aggregate for use in production of the products. ASTM C-33 has defined a specification for a sieve test for aggregate in concrete. The ASTM C-33 procedure passes the aggregate through seven sieves of narrowing sizes (sieve sizes include ⅜", #4, #8, #16, #30, #50, and #100). The test requires that a sample of aggregate be dried and weighed prior to sifting. Drying is accomplished by baking the aggregate for a period of time to reduce to the test's desired moisture content. After the dried sample is weighed, the aggregate is sifted through the seven progressively smaller sieves, and the aggregate collected in each sieve is weighed. The percent collected in each sieve is compared with a passing sample having 100% through ⅜", 95-100% through #4, 80-100% through #8, 50-85% through #16, 25-60% through #30, 5-30% through #50, and 0-10% through #100. In some applications of the test, water may be used to aid in the sifting of the aggregate through the sieves. In this application, the amount of water used is not controlled or collected for observation. In addition, the resulting sorted aggregate must again be dried to the prior moisture content of the previously collected and dried sample to provide an accurate ratio of the sorted components to total sample.

SUMMARY OF THE DISCLOSURE

The subject matter of this application may involve, in some cases, interrelated products, alternative solutions to a particular problem, and/or a plurality of different uses of a single system or article.

One example embodiment of the present invention provides an apparatus including a housing, a plurality of grading screens nested in concentric fashion within the housing, wherein an innermost grading screen defines a receiving compartment configured to receive liquid and/or aggregate, a subsequent grading screen has a finer mesh size and a larger surface area than the innermost grading screen, and a space between adjacent grading screens defines a sorting compartment, and a continuous fluid pathway passing from the receiving compartment through the plurality of grading screens. In some cases, the apparatus includes a lid configured to be brought into a liquid-tight sealing relationship with the housing and the plurality of grading screens. In some other cases, the apparatus includes a lid having disposed therein a plurality of apertures having selective open and closed positions, each of the apertures configured to align with a corresponding sorting compartment and to permit given contents of a given sorting compartment to exit the apparatus, wherein the lid is configured to be brought into a liquid-tight sealing relationship with the housing and the plurality of grading screens. In some still other cases, the apparatus includes a plurality of sorting compartment lids, each such lid configured to be brought into a liquid-tight sealing relationship with a given grading screen, and a housing lid configured to be brought into a liquid-tight sealing relationship with the housing. In some cases, the apparatus includes at least one outlet having selective open and closed positions and configured to permit liquid and/or fines of the aggregate to exit the apparatus when in the open position. In some such cases, at least one such outlet is disposed downstream of the grading screen having the finest mesh size. In some other such cases, at least one such outlet is operatively coupled to at least one sorting compartment. In some cases, fluid communication between adjacent sorting compartments is restricted to occurring through the grading screen there between. In some cases, the apparatus is configured to be tumbled, shaken, spun, or agitated while maintaining the continuous fluid pathway. In some such cases, the apparatus further includes a mechanical agitator configured to perform at least a portion of the tumbling, shaking, spinning, or agitating. In some cases, at least one of the plurality of grading screens has a mesh size that conforms to ASTM C-33 standards. In some cases, at least one of the plurality of grading screens has a shape chosen from the group consisting of cylindrical, conical, polygonal, cuboid, pyramidal, prismatic, and polyhedral. In some cases, the apparatus includes one or more spacers configured to maintain positioning of a first grading screen relative to a second grading screen and/or relative to the housing. In some cases, the apparatus includes an observation container within the housing and configured to collect liquid and/or fines of the aggregate after passage thereof through the plurality of grading screens. In some such cases, the observation container includes indicia for measuring fines in the aggregate and is configured to permit at least one of observing the clarity of the liquid, measuring the volume of settled particulate matter, and/or measuring the turbidity of the liquid. In some cases, the aggregate comprises at least one of powder, dust, clay, sand, gravel, crushed stone, crushed concrete, coal, slag, crushed glass, loam, silt, soil, and/or septic fill.

Another example embodiment of the present invention provides a method of analyzing aggregate comprising passing at least a portion of a liquid and an aggregate through a first grading screen of a given mesh size and a given surface area, passing at least a portion of the liquid and/or the aggregate through a second grading screen, wherein the second grading screen has a finer mesh size and a larger surface area than the first grading screen, and the first grading screen is configured to nest concentrically within the second grading screen, and wherein the first and second grading screens are sealed within a housing, collecting at least a portion of the liquid and/or fines of the aggregate after passage thereof through the second grading screen, and performing at least one of observing the clarity of the collected portion of the liquid, measuring the amount of settled particulate matter in the collected portion of the liquid, measuring the turbidity of the collected portion of the liquid. In some cases, passing at least a portion of the liquid and/or aggregate through a grading screen includes manually tumbling, shaking, spinning, or agitating the housing. In some cases, passing at least a portion of the liquid and/or aggregate through a grading screen includes mechanically tumbling, shaking, spinning, or agitating the housing. In some cases, collecting at least a portion of the liquid involves dispensing liquid and/or fines from an outlet operatively coupled to the grading screens. In some cases, the method further comprises measuring the amount of liquid before and after passage thereof through the aggregate and through one or more of the first and second grading screens. In some cases, the liquid is introduced to the aggregate and is flowed through one or more of the first and second grading screens multiple times and in different directions of flow. In some cases, observing the clarity of the liquid occurs a predetermined period of time after collecting at least a portion of the liquid and/or fines after passage thereof through the second grading screen. In some cases, observing the clarity of the liquid involves comparing its clarity with that of one or more known samples. In some cases, the aggregate comprises at least one of powder, dust, clay, sand, gravel, crushed stone, crushed concrete, coal, slag, crushed glass, loam, silt, soil, and/or septic fill, and wherein observing the clarity of the liquid delineates fines of the aggregate. In some cases, at least a portion of the liquid and/or the aggregate pass through the first and second grading screens in a single step.

Another example embodiment of the present invention provides a system including a grading container comprising a housing, a plurality of grading screens nested in concentric fashion within the housing, wherein an innermost grading screen defines a receiving compartment configured to receive liquid and/or aggregate, a subsequent grading screen has a finer mesh size and a larger surface area than the innermost grading screen, and a space between adjacent grading screens of the plurality defines a sorting compartment, a continuous fluid pathway passing from the receiving compartment and through the plurality of grading screens, wherein fluid communication between adjacent sorting compartments is restricted to occurring through the grading screen there between, and at least one outlet having selective open and closed positions and configured to permit liquid and/or fines of the aggregate to exit the grading container when in the open position, and an observation container configured to receive at least a portion of the liquid and/or fines of the aggregate which exit the grading container via the at least one outlet, wherein the observation container includes indicia for classifying fines in the aggregate and is configured to permit at least one of observing the clarity of the liquid, measuring the volume of settled particulate matter, and/or measuring the turbidity of the liquid.

The systems, devices, and methods described herein may be used separately or together, and components or techniques described in relation to one system or method are capable of being implemented with the others. The subject matter of this application may involve, in some cases, interrelated products, alternative solutions to a particular problem, and/or a plurality of different uses of a single system or article.

BRIEF DESCRIPTION OF THE DRAWINGS

FIGS. 3A-3E are cross-sectional views of an exemplary embodiment of a method and a system for analyzing aggregate.

Figure 1:
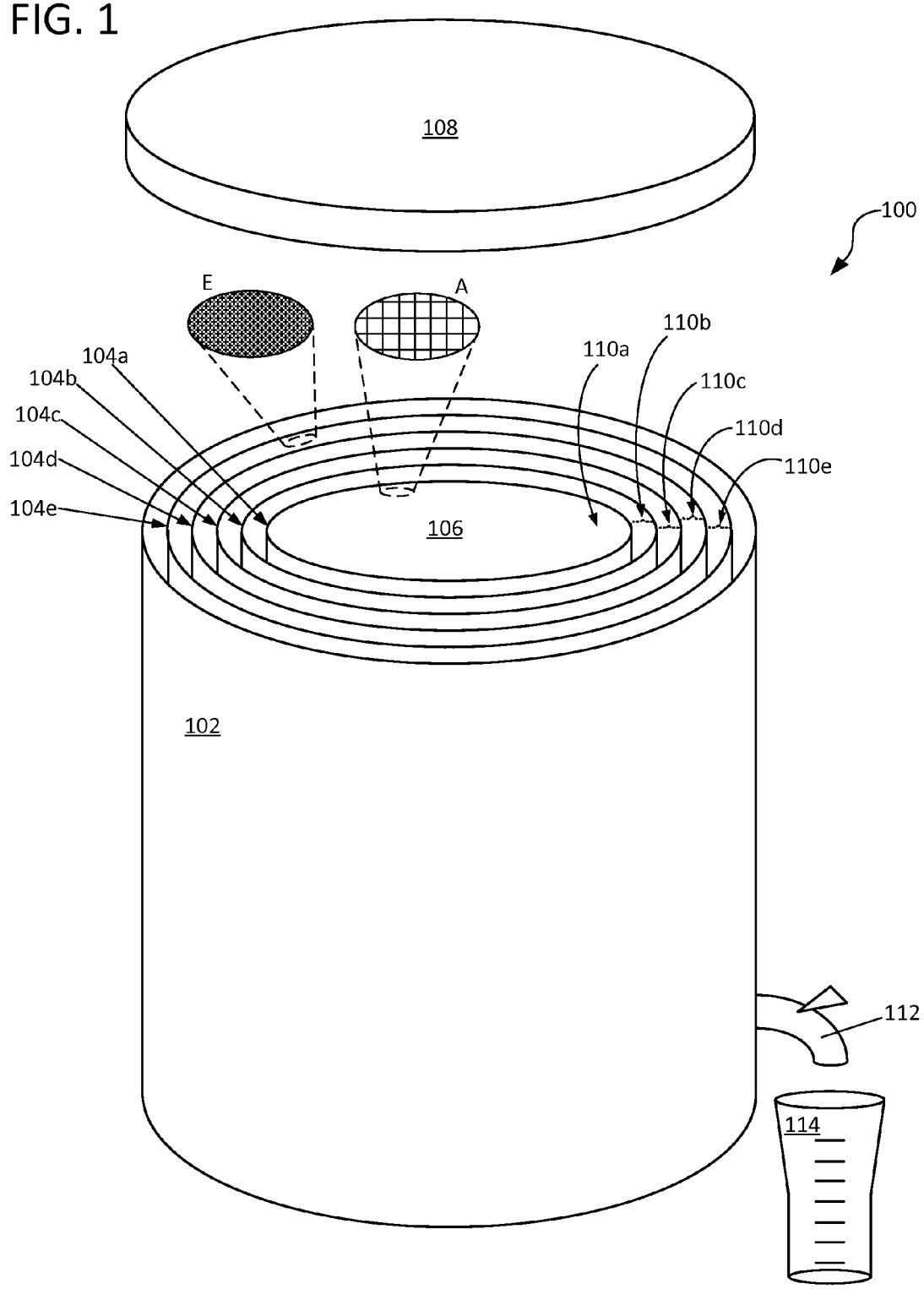
FIG. 1 is a perspective view of an exemplary embodiment of a device for analyzing aggregate.

These and other features of the present embodiments will be understood better by reading the following detailed description, taken together with the figures herein described. The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION

Leach field and septic fill may have specific set requirements for the compositional granularity of the material used. These specific requirements may break down the various granularities of an aggregate into set groups of granular sizes. Failure to follow these specific requirements may result in premature failure of a septic system. In a septic system, digestion of wastewater contaminants may occur by both aerobic and anaerobic digestion. The conditions necessary within a leach field of a septic system are generally aerobic, requiring oxygen. Oxygen needs to flow through the soil to reach the bacteria and waste in the leaching system. When the septic fill contains high levels of fines, the fines may migrate and collect in a layer between the ground surface and the septic discharge. The layer of fines may form dams or low-permeability lenses. These lenses reduce the rate of flow and encourage accumulations of biological material, called "biomats." Biomats can cause clogging of the filter fill material, thus preventing growth of bacteria and effective digestion and deterioration of the effluent. The result is premature failure of the septic system and repair requiring replacement of the filter sand. Minimizing the fines content can inhibit the formation of biomats, but also increases the cost of the sand.

The composition and size of granules of an aggregate material can greatly affect its ability to be used in the production of a particular product. As previously described with respect to septic fill, a fill sand that has too many small particles, referred to in the industry as fines, may result in premature failure of a septic systems. ASTM C-33 has defined standards and specifications for a sieve test for aggregate in concrete. However, these tests may require laboratory conditions. The sample must be collected from the job site and sent to a laboratory for analysis. Construction may be delayed while waiting for laboratory results. Laboratory testing also requires additional time to bake the sample to a desired moisture content. Such analysis may take days to weeks for results from the time of taking the sample to receiving the results at the job site. In addition to the time delay, the laboratory testing also can increase the cost of the project.

The frequency of laboratory testing may be reduced or eliminated due to the cost and time involved. This limited testing may not identify discrepancies that result from shipping or storage of the aggregate. Aggregate composition may change during shipping; for example, the vibrations during transport may cause segregation of particles based on size. Material taken from the top or bottom of a load may have a different particle size composition than what was originally tested and loaded on the vessel. In another example, a pile of stored aggregate also may result in stratification due to exposure to weather and loading/unloading of material. Again, the material taken from the top or bottom of the pile may have a different composition from what was originally mixed and tested before stock piling.

The limited testing also may result in uncertainty in accountability of a manufacturer, shipper, supplier, builder, and end customer. The reputation of a builder may be adversely affected when the correct product was ordered, but due to errors or unscrupulous activity on the part of a member of the supply chain, the wrong product was delivered and used. Likewise, individuals down the supply chain may have their reputation adversely affected by errors or unscrupulous activity on the part of a member up stream. Additional costs may occur when the mistake is discovered after product completion. These additional costs may include demolition and repair costs for the final product far exceeding the original replacement material costs.

Accordingly, embodiments of the invention may provide a device, method, and/or system that allows for more frequent and cost-effective analysis of aggregate composition. Embodiments may allow for composition testing without pre- and/or post-analysis drying of the aggregate. Embodiments may allow for on-site, instant field testing and results. Some embodiments may provide a preliminary test indicating passing results, failing results, or the need for more thorough testing. Embodiments may allow for testing by individuals without formal training or experience. Additionally, embodiments may reduce laboratory tests' costs and time. Some embodiments may supplement or replace current laboratory testing procedures.

Embodiments are not limited to analysis of the compositional granularity of material for leach fields and septic fill. In one example, embodiments may be used to classify soil and/or determine permeability; for example, a soil sample may be analyzed to determine how much silt or loam the sample contains. The analysis may be used, for example, to determine if the soil sample is silty loam or loamy silt. This soil classification may become important when choosing the right septic system product and determining the appropriate system size. Additionally, many industries provide requirements for grading and categorization of fine and coarse aggregate for use in a production of various products. For example, concrete or ceramic producers may have specific set requirements for the compositional granularity of the sand or other components used. These specific requirements may break down the various granularities of an aggregate into specifics ranges of granular sizes. Failure to follow these specific requirements may result in structural defects in concrete or ceramic. Embodiments described herein may be used to analyze the aggregate components used to produce concrete, ceramics, or other materials that include an aggregate component.

In one exemplary embodiment, a device for analyzing aggregate includes one or more grading screens. A port into the device allows for receiving the aggregate and a liquid within the one or more grading screens. The grading screens or sieves may be, for example, but not limited to, screens, mesh, filters, or matrices with selectively sized openings. The screens may include, but are not limited in number or size to, the sieves used in the ASTM C-33 standard (⅜", #4, #8, #16, #30, #50, and #100). The components of the device and the methods of using it also may be customized for other standards or specifications of associations, organizations, or product suppliers or producers; for example, the device can be customized to meet standards set by the American Association of State Highway and Transportation Officials (AASHTO). Embodiments may include additional or fewer screens and/or finer or coarser screens, as may be required. The liquid can form a slurry that can help flush the aggregate through the one or more grading screens and is collected in an observation container. The observation container can be constructed to receive the liquid (including particles), and the liquid then can be analyzed for fines content. Fines content can be determined, for example, by measuring the turbidity of the liquid or by measuring the fines that settle out of suspension.

According to another embodiment, each subsequent, adjacent grading screen from the port for receiving aggregate may have successively finer mesh. The space in between each screen may provide one or more sorting compartments. Passing the aggregate and liquid through successively finer screens allows the coarser/larger granules to be sorted first. As the aggregate and liquid pass through each grading screen, finer and finer aggregate collects in each of the sorting compartments until the final screen of the desired finest mesh size. The successively finer screens may be used not only to filter out the various sized granules, but also to prevent the clogging of material in the first screen encountered. In an embodiment where only the liquid is analyzed for clarity, multiple successively finer screens may allow for efficient filtering of granules even when the the amount of each and every size is not required for analysis. Using only the desired finest screen may result in the assortment of granule sizes forming a dam and obstructing aggregate granules that would have passed through the finest screen. Multiple mesh sizes also can provide valuable information to the operator regarding the particle size distribution of the aggregate being tested.

In another embodiment, the one or more grading screens are housed within a grading container. The grading container may be a liquid-tight container with ports for access. The ports may be opened and closed to allow for receiving and dispensing of aggregate and liquids. The one or more grading screens may be housed within the grading container. The grading container may be sized and configured to allow for easy transport and storage. For example, but without limitation, a 9-inch diameter cylinder with a 12-inch height may provide for easy storage and transportation to the job site. Additionally, the size of the grading container also may allow for an adult human to manually tumble the grading container. Once the aggregate and liquid have been added, the grading container may be shaken back and forth in a tumbling action to allow the liquid to be recycled back through the grading screens and to provide for additional washing of particles through the screens, thus improving the yield of the smallest sized particles, such as fines. The tumbling actions may help to prevent damming of larger particles against a given grading screen, thus enabling smaller particles to more readily reach subsequent, finer screens.

In another embodiment, the device has a receiving compartment for receiving aggregate and liquid from the port, and the device has five successive sorting compartments. In the cylindrical container example, a port may be provided, for example, in the middle of the cylinder, and the port may provide fluid communication between the exterior of the container and the receiving compartment defined by the first (or only) screen. The port may provide the only path to the interior space that is accessible other than through the screen mesh. Cylindrical screens may be provided with successively larger diameter cylindrical screens having finer mesh sizes. The receiving compartment may be provided in the center of the cylindrical container surrounded by the coarser grading screen. The top of the cylindrical container may include a lid to allow access to the receiving compartment. The lid may be removed to allow an individual to add the aggregate sample and liquid to the receiving compartment. A funnel or tube also may be used to provide easy access for receiving aggregate and liquid. It should be noted that, in some embodiments, it may not be required that the liquid be added to the receiving compartment. The liquid may be added through other ports or compartments of the grading container. The grading container may be tumbled to allow circulation of the liquid through the various grading screens, and individual screens may be added or removed independently from the container.

In another embodiment, the device has a receiving compartment for receiving aggregate and liquid from the port, and the device has successive sorting compartments. Each subsequent, adjacent sorting compartment may be separated by grading screens with successively finer meshes. Each sorting compartment may have a dispensing port or other outlet providing access to the respective sorting compartments. In accordance with embodiments that analyze the amount of sorted aggregate by the grading screens, the amount of aggregate collected in each sorting compartment may be dispensed and weighed or used for further analyses. The space formed between successive screens may be the same or varied from screen to screen. As successive screens (smaller mesh sizes as aggregate advances from the interior to the exterior) have larger diameters, the space between screens may be of greater volume as the screen mesh size gets smaller and smaller. Similarly, the screens closest to the exterior of the container may exhibit greater surface area than those near the interior. Thus, the screens having the smallest mesh sizes may be those with the largest surface area. It has been found that this can be advantageous due to a tendency of smaller mesh sizes to clog more readily than the larger mesh sizes. The surface area of the grading screen with the finest mesh size may be 2, 3, 5, or more than 10 times greater than the surface area of the grading screen with the coarsest mesh size, in accordance with an embodiment.

In another embodiment, the receiving compartment may be located in an exterior portion of the device, and the device may have successive sorting compartments advancing inwardly to the interior of the receiving compartment. Each subsequent, adjacent sorting compartment may be separated by grading screens with successively finer meshes (e.g., smaller mesh sizes as aggregate advances from the exterior to the interior). An observation compartment or a dispenser may be located in an interior portion of the device. Embodiments are not limited to successive grading from the interior to the exterior or the exterior to the interior, but may include successive grading screens and sorting compartments located in either a horizontal direction (progressing from top-down) or vertical direction (progressing from side-to-side).

In another embodiment, the final compartment after the final grading screen may include an observation compartment or a dispenser/outlet for dispensing the liquid and any suspended matter into an observation container. It should be noted that the observation compartment/container may be incorporated into the grading container or may be a separate/discrete container. The dispenser/outlet may be, for example, a spigot with a valve. The valve may be placed into a closed position during the adding and tumbling of sample aggregate and liquid. The valve then may be placed into an open position to allow for dispensing of the liquid into the observation container.

In another embodiment, the observation container may allow for observation of the clarity of the liquid after passing through the aggregate and grading screens. According to an exemplary embodiment, the liquid may include fine particles suspended in the liquid. These fine particles, called "fines," are made of clay, stone dust, and organic material. Fines are particles that are generally smaller than about 0.075 millimeters. The liquid may be observed after or prior to a period of settling. For example, the turbidity of the suspension may be measured using a turbidimeter as an indication of the concentration of fine particles suspended in the liquid. Alternatively, the fines may be allowed to settle, providing an observable delineation at an interface between the settled particulate material and the supernatant. If measured prior to settling, the suspension of the particles may be improved by the addition of a dispersion aid such as a dispersant in order to prevent aggregation and maintain the fines in suspension. If segregation of the particles from the liquid is desired, a settling agent such as a flocculant may be used. This may accelerate the settling of the particles, thereby allowing a faster determination of fine particles content. The observation container also may include markings/indicia to aid in classifying the fines in the aggregate.

An exemplary embodiment may include a method for analyzing aggregate. The aggregate may be placed within one or more grading screens. A carrier liquid is passed through the aggregate and one or more grading screens. After passing the carrier liquid through the aggregate and one or more grading screens, the liquid is collected and observed. The clarity of the observed liquid may be used to analyze the liquid. The cloudiness or clarity of the liquid may be used to determine the fines in the aggregate. In one exemplary embodiment, the analysis may be used as a screening test. For example, a screening test may indicate that the aggregate is well within the acceptable standards or that the aggregate is well outside of the acceptable standards and should not be used. Another category may indicate that further testing may be needed prior to use of the aggregate, and this may be followed by a laboratory test.

According to another embodiment, the method may use a grading container housing multiple sorting compartments with each sorting compartment separated by the one or more grading screens. In another embodiment, the action of collecting the suspension may involve dispensing liquid from a port of the grading container housing.

According to another embodiment of the method, the method may use a set amount of aggregate sample and liquid; for example, the method may use one cup of aggregate and two cups of water. After passing the liquid through the aggregate and one or more grading screens one or more times, a set amount of liquid also may be collected. For example, a test may require that at least one and a half cups of liquid of the two cups placed in the grading container must be collected in the observation container.

According to another embodiment, the action of passing liquid involves passing the liquid through the aggregate and one or more grading screens multiple times. This may involve, for example, a pump or tubing that allows for the recirculation of liquid back through the aggregate and one or more grading screens. This also may involve a tumbling, agitating, spinning, or shaking of a grading container allowing the liquid to pass back and forth through the grading screens. Some embodiments may require a set/predetermined amount of time for tumbling of the grading container; for example, five to ten minutes. Other embodiments may involve a device to facilitate the tumbling; for example, a motor or crank-operated device may be used to cause the grading container to vibrate, shake, agitate, and/or tumble. Furthermore, in some embodiments, the action of passing liquid may involve movement of the grading container in an orbital fashion and/or may involve spinning or precessing of the grading container.

According to another embodiment, the method may involve the analysis of the amount of aggregate sorted in each sorting compartment between grading screens. In one embodiment, the contents of each sorting compartment may be measured, for example, by weighing and recorded. The recorded amount may be compared with the weight of the original sample, the weight of the original liquid added, and the weight of the liquid collected in the observation container. This data then may be used to calculate the percentage of aggregate collected in each sorting compartment.

According to another embodiment, the action of observing the clarity of the liquid may occur a set/predetermined period of time after the action of collecting the liquid. In one example, the period may be a set time between five and ten minutes, between ten and twenty minutes, or between twenty and thirty minutes, or longer. This may allow at least some of the fines to settle to the bottom of the observation container. The analysis may involve measuring the height of a settled layer or a comparison of multiple layers within the liquid. In one example, the markings/indicia may indicate the maximum height allowed for the layer of settled fines in order for the tested sample to meet specifications. In another example, the analysis may involve markings indicating the maximum height allowed for cloudy liquid. In this example, a clear liquid layer may be required above an indicative mark. Embodiments are not limited by settling time and may include centrifuging or addition of coagulant or flocculating agents. Embodiments also are not limited to analysis by markings/indicia on the observation container. In one embodiment, the clarity of the observation container may be compared with known samples including liquid with known amounts of fines. In this example, both the collected sample and standard samples may be shaken at the same time and immediately compared to determine which known sample the collected sample best matches. Based on this comparison, the amount of fines may be determined quantitatively or on a pass/failure basis. Accordingly, the amount of fines in a test of aggregate may be determined empirically based on a comparison with known samples of acceptable aggregate. In another exemplary embodiment, a device for measurement of light transmission or light scattering, such as a turbidimeter, may be used to analyze the collected liquid.

Referring to FIG. 1, an exemplary device 100 for analyzing aggregate may include a grading container 102. Grading container 102 may house or otherwise contain one or more grading screens 104a-104e. As shown in expanded views A and E, the grading screen 104e may have finer mesh than the grading screen 104a. Each of the grading screens 104a-104e may have successively finer screens starting with the grading screen 104a and progressing through to grading screen 104e. Embodiments are not limited to five grading screens and may have more or less than five grading screens. A receiving compartment 106, which may be located in the middle of the grading container 102, may be used to load the aggregate sample and liquid. Once loaded, the lid 108 may be placed on the grading container 102. The lid may provide a seal between the grading screens 104 and the grading container 102, thus preventing any aggregate and liquid from passing to other compartments without passing through the various grading screens 104. As the aggregate and liquid mix and pass through the various grading screens, the aggregate is sorted into the various sorting compartments 110a-110e. Once thoroughly mixed, the liquid may be dispensed into an observation container 114 through spigot 112. The spigot 112 may be selectively opened or closed. During mixing or tumbling, the spigot 112 may be closed to retain the liquid within the grading container 102. Once the tumbling process is complete, the spigot 112 may be opened to dispense the liquid and any suspended particles into the observation container 114.

Figure 2:
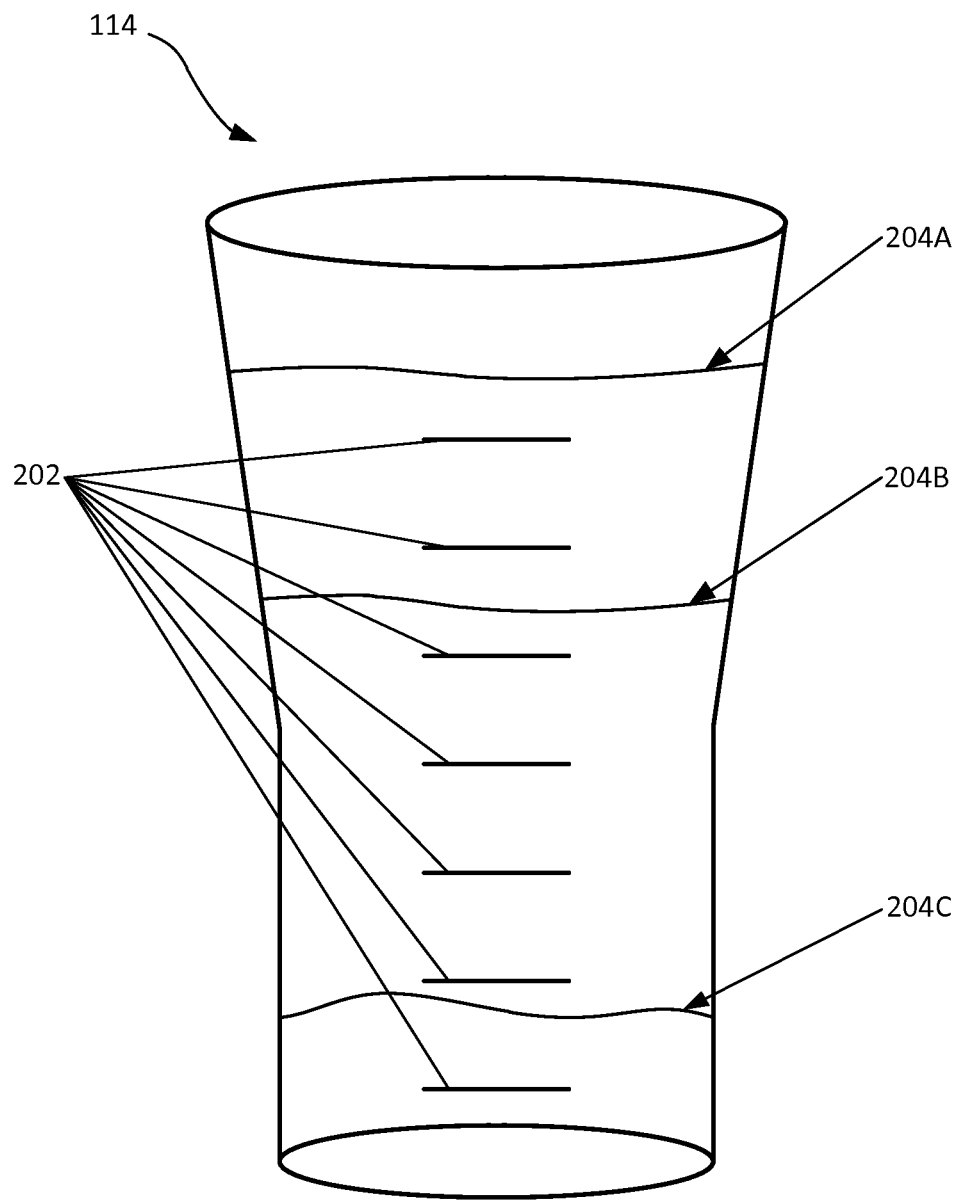
FIG. 2 is a perspective view of an exemplary embodiment of an observation container for analyzing liquid.

Referring to FIG. 2, an exemplary observation container 114 is filled with liquid dispensed from the grading container 102. Observation container 114 may be a transparent container with markings 202 to aid the user in analysis. In one embodiment, markings 202 may be used to indicate the desired amount of liquid to be dispensed into the observation container 114. For example, the top markings 202 may indicate the level that the liquid 204A should meet. In other embodiments, the markings may indicate the acceptable level of, for example, settled fines 204C after a set period of time or level of acceptable cloudiness of the supernatant liquid 204B. In another embodiment, the markings 202 may be viewed from the opposite side of the container. In this embodiment, the markings may be used to indicate levels of cloudiness. For example, the user looking through the observation container 114 at the markings 202 on the opposite side of the observation container 114 may gauge the cloudiness by indicating the lowest marking 202 that is observable with the naked eye. In another embodiment, the liquid, including suspended fines, can be transferred to a vial or cuvette that can then be read using a turbidimeter, such as a model 2100Q Portable Turbidimeter available from Hach Corporation. The amount of fines in the original aggregate sample then can be correlated to the turbidity of the liquid suspension.

Figure 3E:
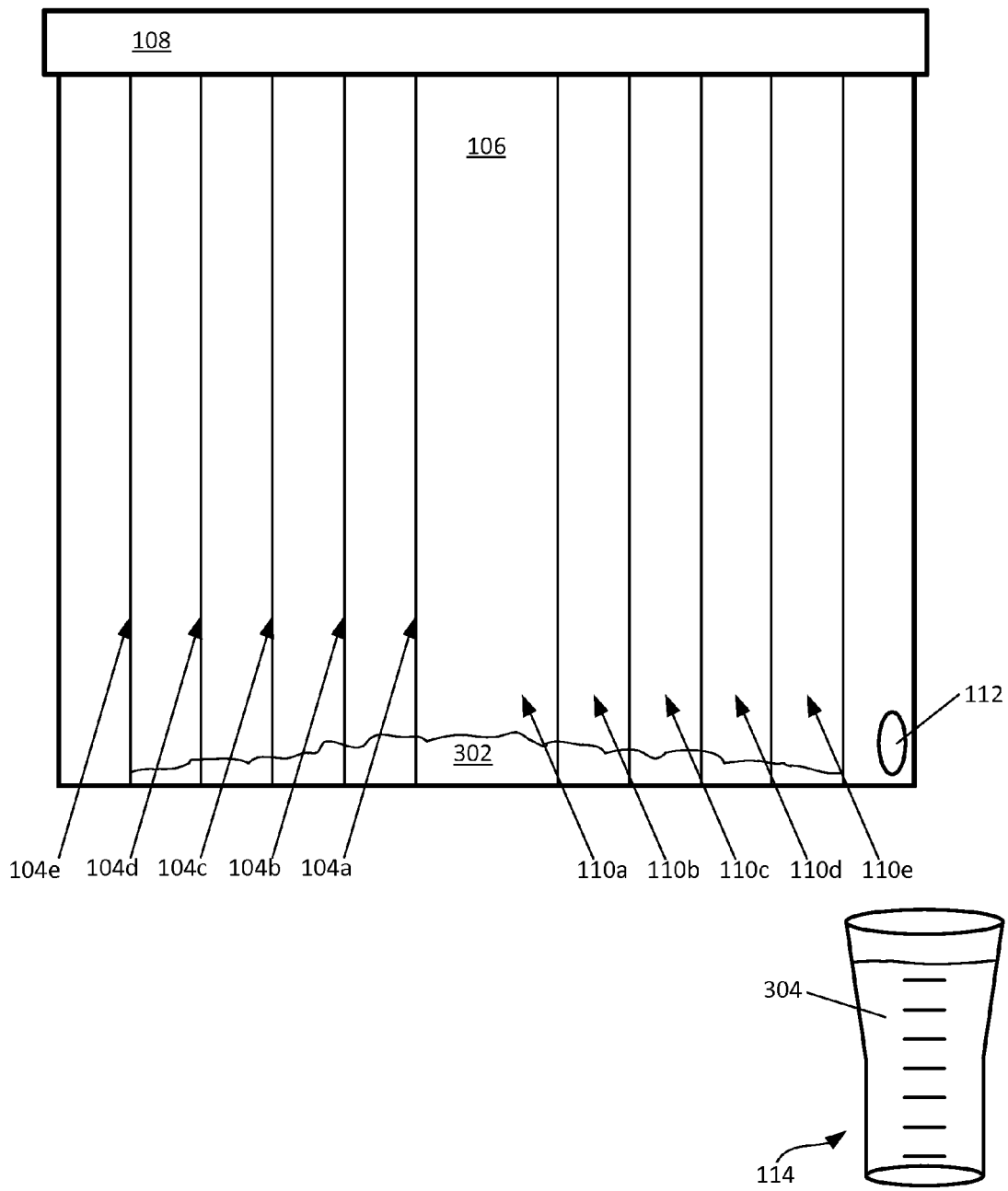

Referring to FIGS. 3A-3E, an exemplary method and system for analyzing aggregate is provided. Beginning with FIG. 3A, a cross-section view of the grading container 102 is shown. The sample aggregate 302 and liquid 304 are collected and prepared for analysis. The preparation may involve measuring the sample, as well as various other methods, to ensure an accurate sample has been collected. The sample may be measured either volumetrically or by mass. Referring to FIG. 3B, the aggregate sample 302 is dumped into the receiving compartment 106 of the grading container 102. Referring to FIG. 3C, the liquid 304 also is placed into the receiving compartment 106. The liquid 304 and aggregate sample 302 are combined and mixed in the receiving compartment 106. The liquid 304 may aid in the aggregate 302 sifting and passing through the various grading screens 104. Referring to FIG. 3D, the lid 108 may be secured on the grading container 102, providing a liquid-tight seal with both the outside container and the individual grading screens 104. The mixture of aggregate 302 and liquid 304 is tumbled in a rocking motion to aid in the aggregate sifting process. The tumbling action may cause the liquid to recirculate through the grading screens 104. The recirculated liquid 304 may break up dams formed by the aggregate 302 and grading screens 104. The liquid 304 may suspend granules of the aggregate 302 facilitating passage of the grading screens 104 and into the correct sorting compartment 110 based on the size of the granule. Referring to FIG. 3E, the liquid 304 with suspended fines that have made it through all of the grading screens 104 may then be drained through the spigot 112 and into the observation container 114. The spigot 112 may be located on or near the bottom of the grading container 102 to aid in drainage of the liquid out of the grading container. The user also may tilt the grading container during drainage to facilitate the drainage of liquid 304 out of the spigot 112. Additionally, the device may incorporate additional features to facilitate drainage of the liquid 304; for example, the bottom surface may be sloped in the direction of the spigot 112. The spigot 112 also is not limited to a lower side location. The spigot 112 may be located, for example, on the top or bottom surface of the device. The liquid 304 and suspended material may be analyzed further in the observation container 114, as previously discussed in other embodiments.

Figure 4:
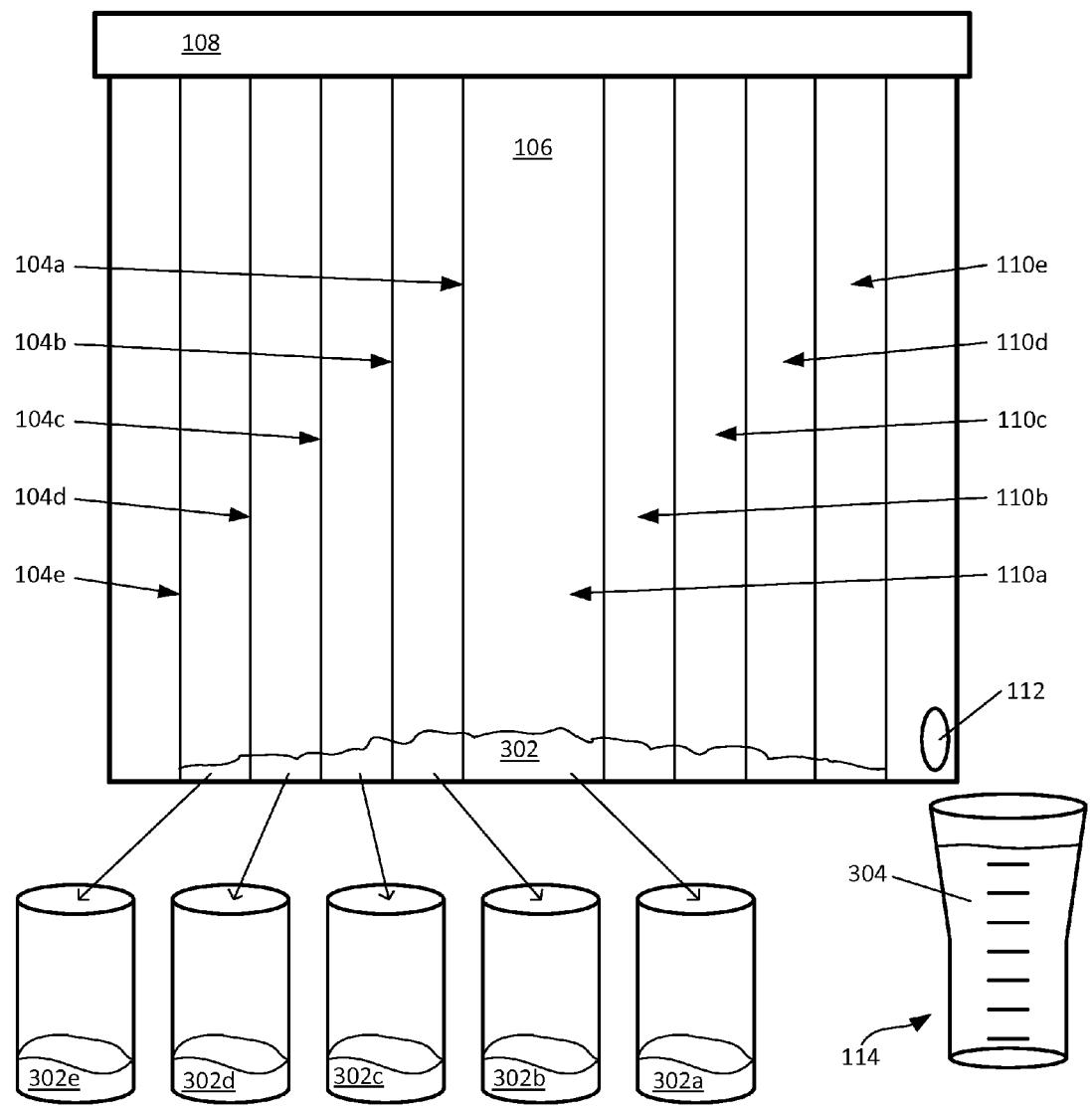
FIG. 4 is a cross-sectional view of another exemplary embodiment of a system for analyzing the liquid and sorted aggregate.

Referring to FIG. 4, the various sorted components of the aggregate may be analyzed further. The aggregate components may be emptied from each of the sorting compartments 110. Each sorted aggregate component 302a-302e may be analyzed further to determine, for example, the percentage relative to the total sample taken. This information may be used independently or in conjunction with the analysis of the liquid sample. It should be noted that the receiving compartment 106 also may be used as a sorting compartment 110a for the coarser materials.

Figure 5A:
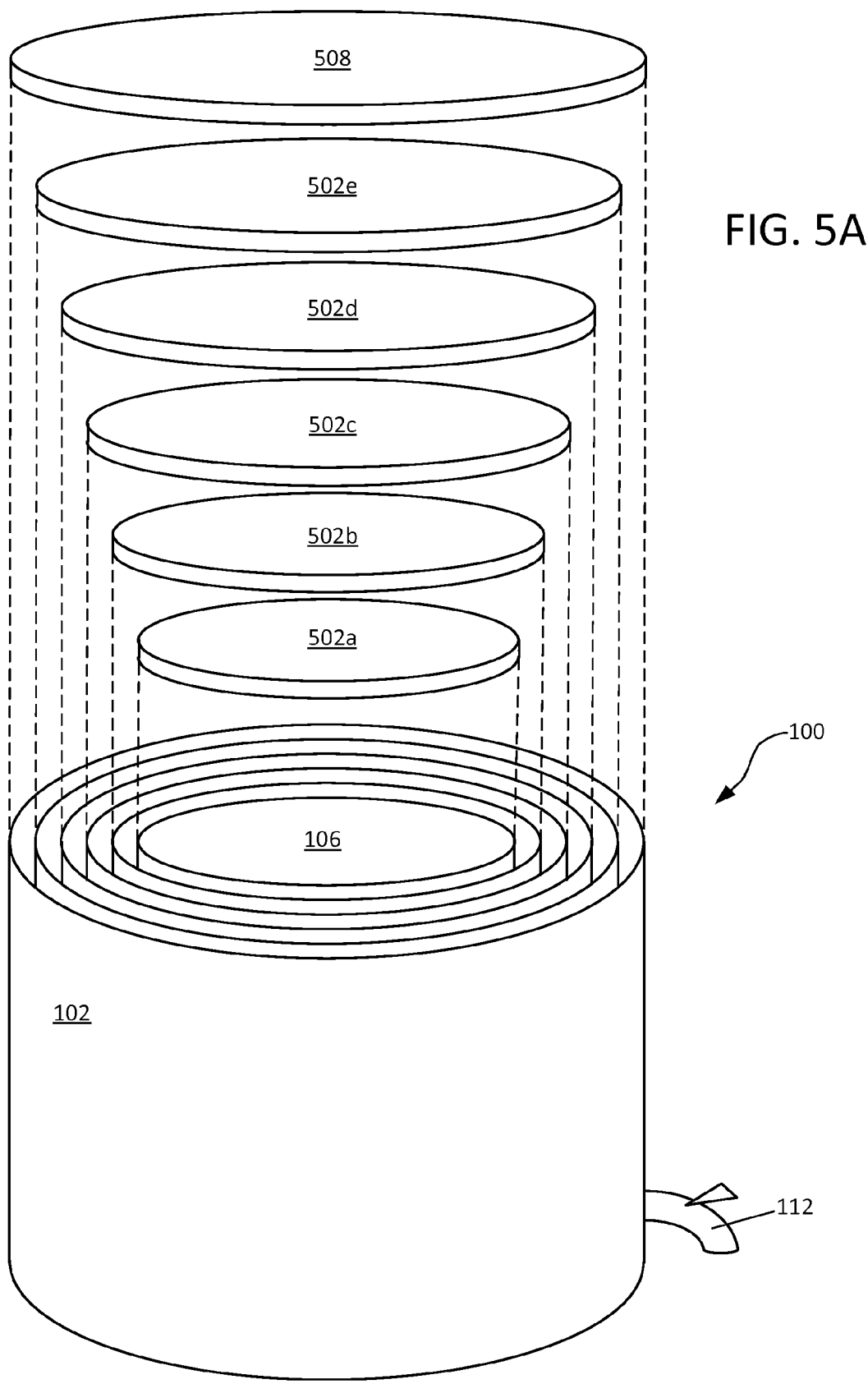
FIG. 5A is a perspective view of another exemplary embodiment of a device for analyzing aggregate having separate sorting compartment lids.
Figure 5B:
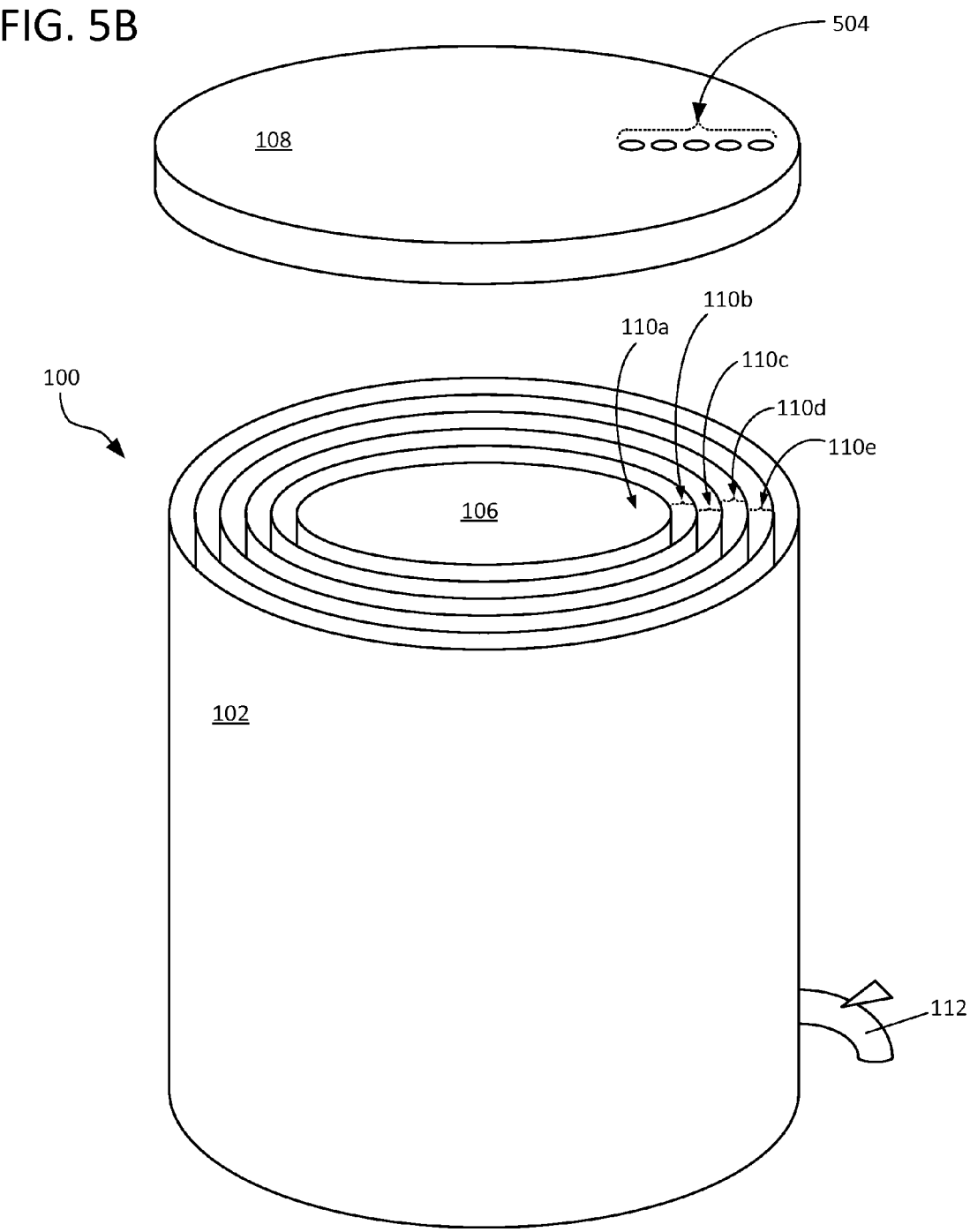
FIG. 5B is a perspective view of another exemplary embodiment of a device for analyzing aggregate having separate sorting compartment portals.

Referring to FIGS. 5A and 5B, the grading container 102 is not limited to the lid 108 as described in earlier embodiments. The lid may be a combination of several lids 508 and 502a-502e, for example, to aid in the removal of sorted aggregate components after mixing. In FIG. 5A, individual lids 502a-502e are provided for each grading screen 104 and attendant sorting compartment 110 (e.g., lid 502a corresponds with sorting compartment 110a defined by grading screen 104a). To place the aggregate sample in the grading container 102, all the lids 508 and 502a-502e, for example, are removed. After the aggregate sample and liquid are added to the receiving compartment 106, the lids 502a-502e are fitted onto the respective individual sorting compartments 110a-110e, and lid 508 is then fitted onto grading container 102. After mixing and drainage of the liquid, the lid 508 is first removed and then each lid 502a-502e for each sorting compartment 110a-110e is removed as each sorted component is removed and placed into a specimen container. Each lid 502a-502e may provide a liquid-tight or an adequate seal to prevent contamination between the various sorting compartments 110. Each grading screen 104 may be, for example, a cylindrical shape with side walls and bottom of the respective grade screen. Each individual grading screen 104 may be removed from the grading container 102 to facilitate emptying of the various sorted components of aggregate. Accordingly, spacers or brackets may be provided to allow space between the bottoms of each successive grading screen 104 as well as to the final grading screen 110 and the bottom of the grading container 102. It should be noted that each sorting compartment/container may be incorporated into a grading container or may be separate containers that couple together.

Referring to FIG. 5B, another embodiment may provide individual ports/apertures 504 on the lid 108 for each sorting compartment 110. After mixing and sorting the aggregate sample, each individual port may be opened to allow emptying of the respective sorting compartments 110. Embodiments are not limited to these ports or dispensing port/spigot 112. Other ports/outlets may be provided to facilitate the process. For example, the grading container 102 may include a flush port for flushing tested aggregate and liquid from the grading container 102 after testing, thus preventing the contamination of future test samples with material from prior test samples.

Figure 6:
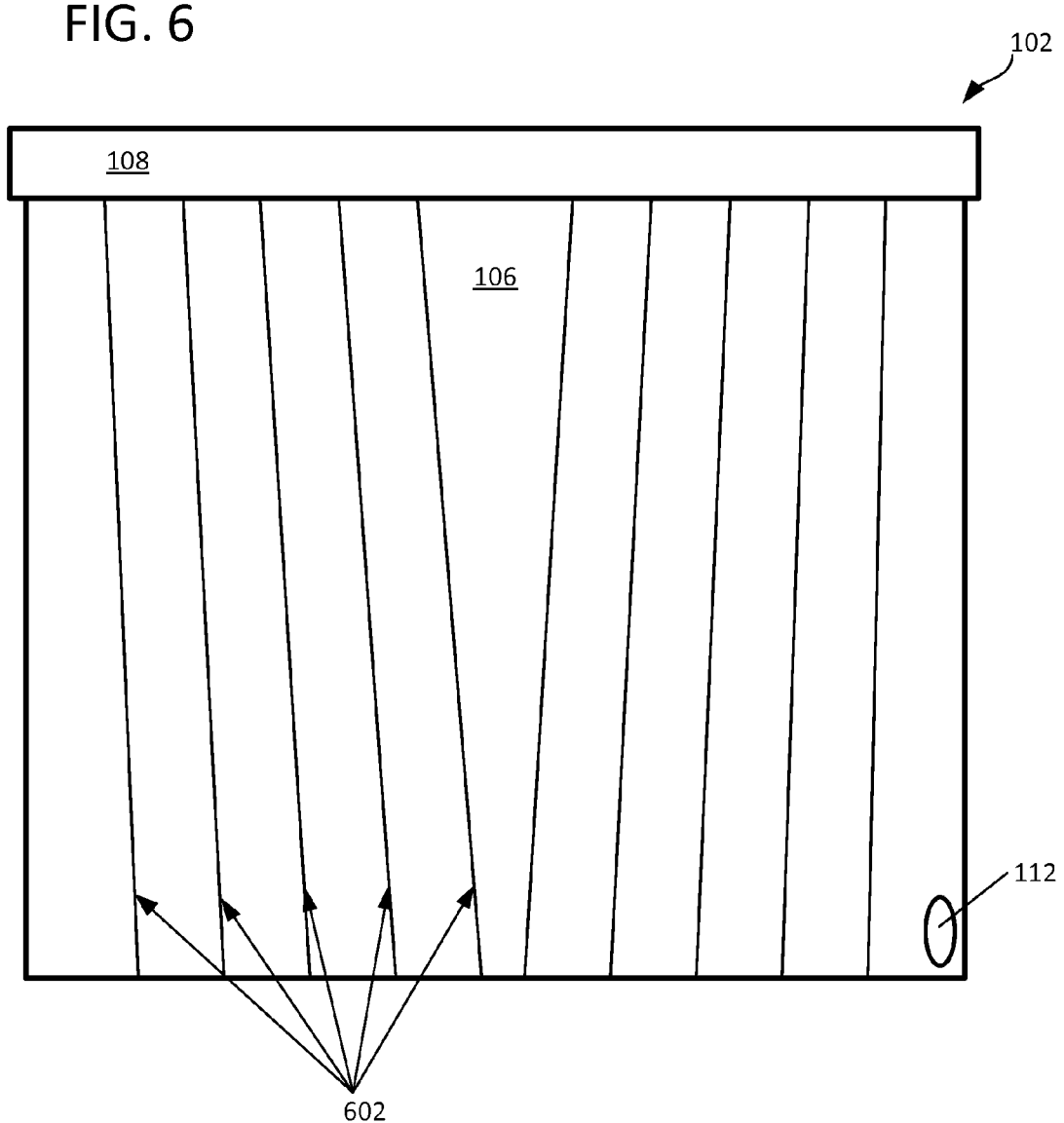
FIG. 6 is a cross-sectional view of another exemplary embodiment of a device for analyzing aggregate having conical shaped grading screens.

Referring to FIG. 6, the sample of the grading screens 104 is not limited to a cylindrical shape. According to another embodiment, the grading screens 602 may be conical shaped having tapered walls with a narrower bottom relative to the top. Embodiments are not limited to the angles shown. For instance, the grading screens 104 may be any suitable shape, such as, but not limited to: cylindrical, conical, polygonal, cuboid, pyramidal, prismatic, or polyhedral, or any two-dimensional variation/derivative of such geometries.

Figure 7:
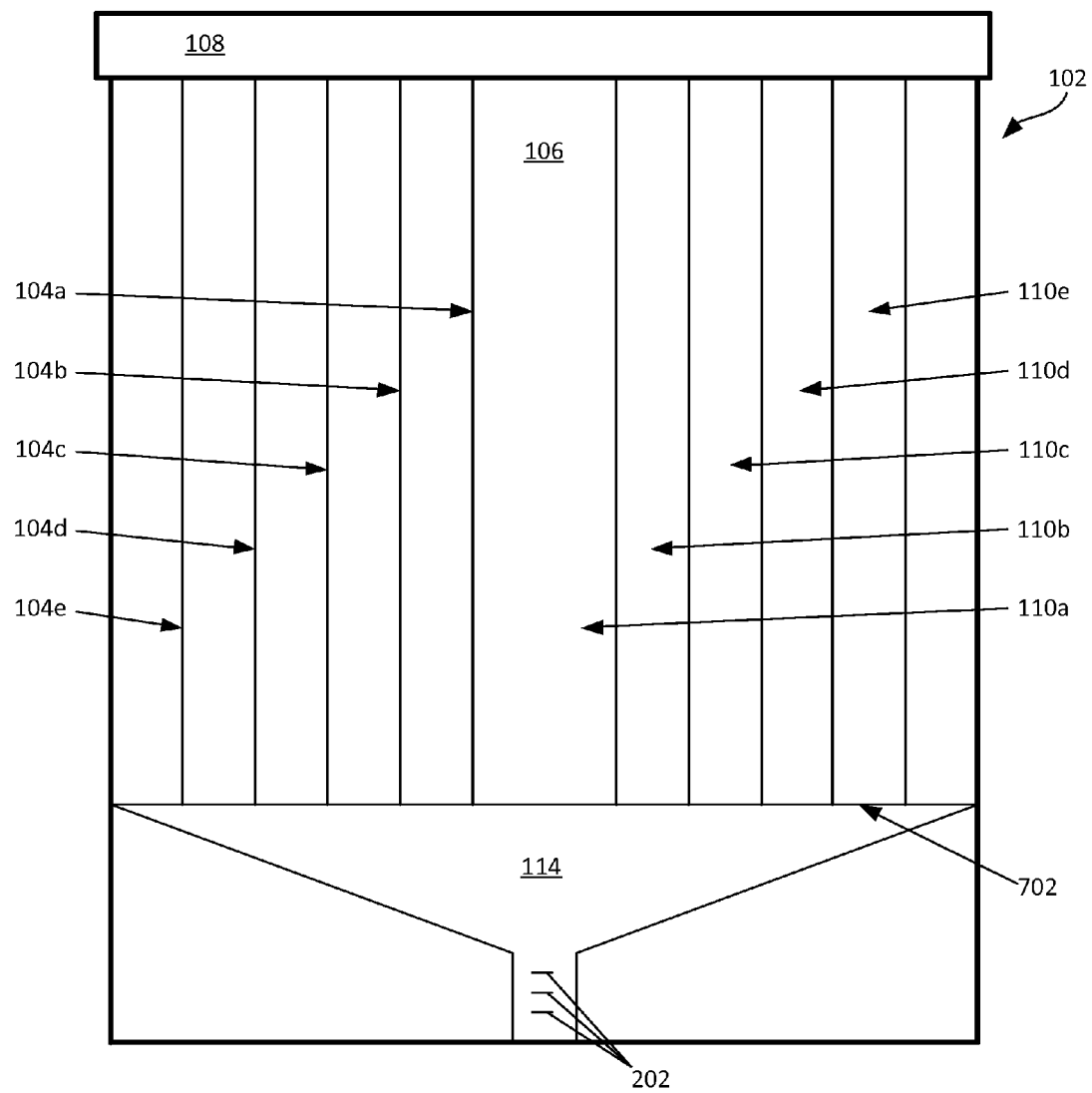
FIG. 7 is a cross-sectional view of another exemplary embodiment of a device for analyzing aggregate having a grading and observations containers within the same housing.

Referring to FIG. 7, an exemplary device 700 for analyzing aggregate may include a grading container 102 and observation container 114 within the same housing. Similar to previously described embodiments, within the grading container 102 are one or more grading screens 104a-104e. Each of the grading screens 104a-104e may have successively finer screens starting with the grading screen 104a and progressing through to grading screen 104e. The receiving compartment 106 may be used to load the aggregate sample and liquid. Once loaded, the lid 108 may be placed on the grading container 102. As the aggregate and liquid mix and pass through the various grading screens, the aggregate is sorted into the various sorting compartments 110a-110e. Once thoroughly mixed, the liquid may be dispensed into an observation container 114 through a separating device 702. The separating device 702 may be a plate designed to prevent the liquid from entering the observation container 114 until after mixing of the aggregate and liquid. Once mixed, the plate may be removed to allow the liquid to drain into the observation container 114. In another example, the separating device 702 may be a port with a valve. In yet another example, the separating device may be a screen allowing the liquid to enter and circulate through the observation container 114 during the mixing process. Once the mixing process is complete, the liquid may be allowed to settle through the sorting compartments 110a-110e and into the observation container 114.

As previously described, the exemplary observation container 114 may be a transparent vessel with markings 202 to aid the user in analysis. The amount of fines in the original aggregate sample then can be measured by viewing the height of the sediment in the marked portion of observation container 114. In other embodiments, the turbidity of a suspension can be measured by shining light through observation container 114. The observation container 114 may include inclined walls or floors to facilitate the draining of the liquid and fines. The observation container 114 may be integral to the same housing as the grading container 102 and is not limited to the location as shown in FIG. 7; for example, the observation container 114 may be located on an outer wall of the housing 700. As those of ordinary skill in the art will readily envision, the observation container 114 may be positioned in a variety of locations within the housing 700.

According to another embodiment, the device for analyzing aggregate is not limited to the portable device as described in other exemplary embodiments. The device for analyzing aggregate may be incorporated into a fully or partially mechanized or automated device. Such device may allow for minimal or no human interaction. Exemplary devices may control the specific amounts of aggregate or liquid analyzed and/or control the distribution or cycling of liquid through the aggregate. Additionally, the observation of liquid or aggregate also may be automated using optical, electrical, or mechanical analysis. The device for analyzing aggregate also is not limited to the size and shape as described in other exemplary embodiments. Exemplary devices may perform analysis on a large scale; for example, testing large amounts of aggregate and/or performing multiple analyses in rapid succession. Exemplary devices may be incorporated into production/manufacturing line equipment that may test aggregate automatically and routinely in a continuous manner during the production or manufacturing process.

Figure 8:
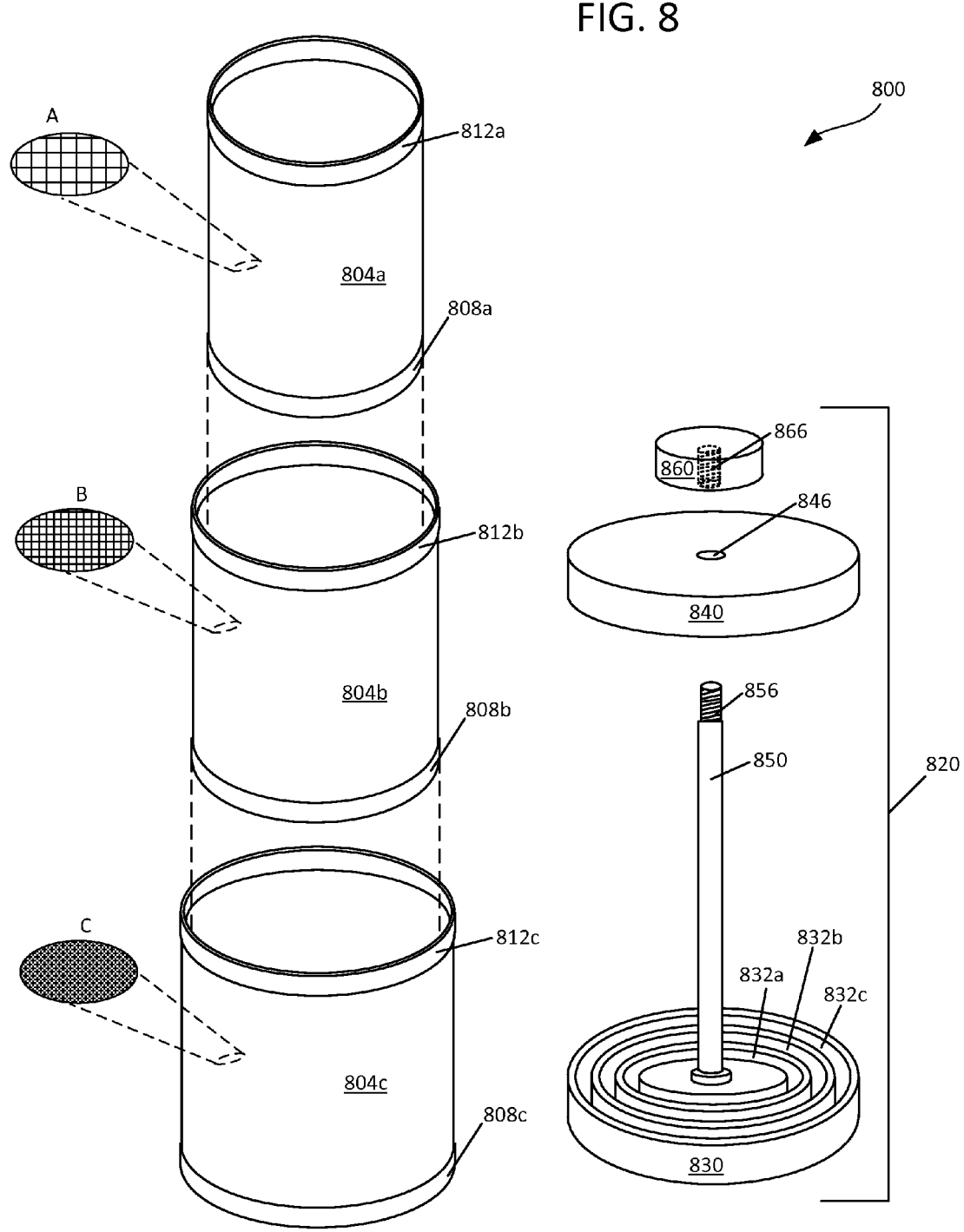
FIG. 8 is an exploded perspective view of another exemplary embodiment of a device for analyzing aggregate having grading screens featuring overmolded portions and a corresponding insert.

Referring to FIG. 8, an exemplary device 800 for analyzing aggregate may include one or more grading screens 804a-804c and an assembly 820 configured to receive/secure the grading screens 804a-804c. As shown by expanded views A, B, and C, grading screen 804c may have finer mesh than grading screen 804b, which may have finer mesh than grading screen 804a. As similarly discussed previously in the context of other embodiments of the present invention, each of grading screens 804a-804c may have successively finer screens starting with grading screen 804a and progressing through to grading screen 804c (or further subsequent grading screen). Embodiments are not limited to three grading screens and may have more or less than three gradings screens (e.g., five grading screens). Grading screens 804a-804c may be configured to nest in concentric fashion, with the innermost grading screen having the coarsest mesh size and subsequent grading screens having progressively finer mesh sizes. Other suitable arrangements/configurations will depend on a given application and will be apparent in light of this disclosure.

As can be seen in the figure, and in accordance with a specific example embodiment, a grading screen 804a may include a thickened or otherwise broadended edge; for instance, a first overmolded portion 808a formed on a bottom/first edge thereof and/or a second overmolded portion 812a formed on a top/second edge thereof. Additional grading screens may be similarly configured (e.g., grading screen 804b with one or more overmolded portions 808b/812b, grading screen 804c with one or more overmolded portions 808c/812c, etc.). In some such cases, the overmolded portions may assist with, for example: (1) fitting/securing a given grading screen with end plates 830 and/or 840; (2) maintaining the spacing between two consecutive grading screens (e.g., maintaining the dimensions of a given sorting compartment defined therebetween); and/or (3) ensuring that liquid and/or aggregate is prevented from passing from one sorting compartment to another sorting compartment other than by flowing through a given grading screen.

Assembly 820 may be configured to receive/secure the one or more grading screens 804a-804c. In some cases, assembly 820 may comprise, for example, a first end plate 830, a second end plate 840, a connector 850, and a securing mechanism 860. In some instances, assembly 820 may be configured/sized to be positionable within a grading container 102 or other suitable receptacle, as previously discussed.

The one or more end plates 830/840 may be configured to receive and/or secure grading screens 804a-804c. For instance, end plates 830/840 may include one or more ribs, tabs, recesses, protrusions, tracks, or other suitable features defined therein/thereon which allow for a mated/sealed relationship with the overmolded portions 808a-808c and/or 812a-812c of the grading screens 804a-804c. In one specific example embodiment, end plate 830 includes a plurality of concentrically arranged recessed tracks 832a-832c configured to receive overmolded portions 808a-808c, and end plate 840 is similiarly configured with a plurality of concentrically arranged recessed tracks (not visible in the figure) configured to receive overmolded portions 812a-812c. In some such instances, this configuration may help to ensure that the grading screens 804a-804c remain securely positioned/spaced, thus ensuring that liquid and/or aggregate is prevented from passing from one sorting compartment to another sorting compartment other than by flowing through a given grading screen. Other suitable configurations which achieve this aim will be apparent in light of this disclosure.

Assembly 820 may include a connector 850 configured to join/space end plates 830 and 840. Grading screens 804a-804c may be positionable about connector 850; for example, grading screens 804a-804c may be positioned in concentrically nested fashion about a connecting rod 850. In one example case, end plate 840 may include an aperture 846 configured to accommodate connector 850. Depending on a given application, connector 850 may be appropriately configured to provide a joining/interlocking connection between end plate 830 and end plate 840 (and thus help to secure the positioning of the one or more grading screens 804a-804c), and may provide, for example: a threaded connection, a snap fit connection, a ball lock connection, a detent pin connection, a bayonet mount connection, a twist lock connection, a cotter pin connection, or a retaining clip connection. Other suitable configurations for connector 850 will be apparent in light of this disclosure.

Assembly 820 may include a securing mechanism 860 (e.g., a cap, nut, plate, etc.) including a portion 866 configured to interlock with or otherwise securely engage a portion 856 of connector 850. For instance, in one specific example embodiment, securing mechanism 860 includes a threaded, recessed portion 866 configured to engage a threaded, screw-type protrusion 856 of connector 850.

As will be appreciated in light of this disclosure, any of the components of the various embodiments of the device for analyzing aggregate may be formed using techniques such as, but not limited to, thermoset molding, injection molding, or other suitable manufacturing/production techniques. In some embodiments, one or more components of the device may be formed, for example, from materials such as, but not limited to, polypropylene, polyethylene, acrylic, or other suitable material or combination of materials.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

The term "aggregate" is used herein to describe solid material having the same or an assortment of different sized granules or particulate matter, for example, but not limited to, powder, dust, clay, sand, gravel, crushed stone, crushed concrete, coal, slag, crushed glass, loam, silt, and soil. Granules and particles are not limited to naturally occurring, manufactured, or a combination.

The aggregate may be, for example, natural or synthetic packed aggregate. Natural aggregates may further include, for example, crushed stone and sand.

The term "liquid" is used herein to describe a substance in a fluid state, for example, but not limited to, water, oils, alcohols, or solvents. The liquid also may include coagulant agents, toxic agents, and/or filtering agents.

All references, patents and patent applications and publications that are cited or referred to in this application are incorporated in their entirety herein by reference.

What is claimed is:

1. An apparatus comprising:
  a housing;
  a plurality of grading screens nested in concentric fashion within the housing, wherein an innermost grading screen defines a receiving compartment configured to receive aggregate, a subsequent grading screen has a finer mesh size and a larger surface area than the innermost grading screen, and a space between adjacent grading screens defines a sorting compartment;
  a continuous fluid pathway passing from the receiving compartment through the plurality of grading screens;
  a first end plate configured to engage a first end of the plurality of grading screens;
  a second end plate configured to engage a second end of the plurality of grading screens;
  a connector extending between and joining the first end plate and the second end plate, wherein the connector resides within the receiving compartment of the innermost grading screen; and
  a lid configured to be brought into a liquid-tight sealing relationship with the housing;
  wherein at least one of the first end plate or second end plate is further configured to be brought into a liquid-tight sealing relationship with the plurality of grading screens.

2. The apparatus of claim 1, wherein the lid has disposed therein a plurality of apertures having selective open and closed positions, each of the apertures configured to align with a corresponding sorting compartment and to permit contents of a given sorting compartment to exit the apparatus.

3. The apparatus of claim 1 further comprising at least one outlet having selective open and closed positions and configured to permit liquid and fines of the aggregate to exit the apparatus when in the open position.

4. The apparatus of claim 3, wherein at least one such outlet is disposed downstream of the grading screen having the finest mesh size.

5. The apparatus of claim 1, wherein fluid communication between adjacent sorting compartments is restricted to occurring through the grading screen there between.

6. The apparatus of claim 1, wherein the apparatus is configured to be tumbled, shaken, spun, or agitated while maintaining the continuous fluid pathway.

7. The apparatus of claim 6, wherein the apparatus further comprises a mechanical agitator configured to perform at least a portion of the tumbling, shaking, spinning, or agitating.

8. The apparatus of claim 1, wherein at least one of the plurality of grading screens has a mesh size that conforms to ASTM C-33 standards.

9. The apparatus of claim 1, wherein at least one of the plurality of grading screens has a shape chosen from the group consisting of cylindrical, conical, polygonal, cuboid, pyramidal, prismatic, and polyhedral.

10. The apparatus of claim 1 further comprising one or more spacers configured to maintain positioning of a first grading screen relative to a second grading screen or relative to the housing.

11. The apparatus of claim 1, wherein the aggregate comprises at least one of powder, dust, clay, sand, gravel, crushed stone, crushed concrete, coal, slag, crushed glass, loam, silt, soil, or septic fill.

12. A method of analyzing aggregate, the method comprising:
  passing at least a portion of a liquid and an aggregate through a first grading screen of a given mesh size and a given surface area;
  passing at least a portion of the liquid and the aggregate through a second grading screen, wherein the second grading screen has a finer mesh size and a larger surface area than the first grading screen, and the first grading screen is configured to nest concentrically within the second grading screen, and wherein the first and second grading screens are sealed within a housing;
  collecting at least a portion of the liquid and fines of the aggregate after passage thereof through the second grading screen; and
  performing at least one of:
    observing the clarity of the collected portion of the liquid;
    measuring the amount of settled particulate matter in the collected portion of the liquid; or
    measuring the turbidity of the collected portion of the liquid;
  wherein passing at least a portion of the liquid and aggregate through a grading screen comprises tumbling, shaking, spinning, or agitating the housing.

13. The method of claim 12, wherein tumbling, shaking, spinning, or agitating of the housing is performed manually.

14. The method of claim 12, wherein tumbling, shaking, spinning, or agitating of the housing is performed mechanically.

15. The method of claim 12, wherein collecting at least a portion of the liquid involves dispensing liquid and fines from an outlet operatively coupled to the grading screens.

16. The method of claim 12 further comprising measuring the amount of liquid before and after passage thereof through the aggregate and through one or more of the first and second grading screens.

17. The method of claim 12, wherein the liquid is introduced to the aggregate and is flowed through one or more of the first and second grading screens multiple times and in different directions of flow.

18. The method of claim 12, wherein observing the clarity of the liquid occurs a predetermined period of time after collecting at least a portion of the liquid and fines after passage thereof through the second grading screen.

19. The method of claim 12, wherein the aggregate comprises at least one of powder, dust, clay, sand, gravel, crushed stone, crushed concrete, coal, slag, crushed glass, loam, silt, soil, or septic fill, and wherein observing the clarity of the liquid delineates fines of the aggregate.

20. The method of claim 12, wherein at least a portion of the liquid and the aggregate pass through the first and second grading screens in a single step.

21. A system comprising:
  a grading container comprising:
    a housing;

a plurality of grading screens nested in concentric fashion within the housing, wherein an innermost grading screen defines a receiving compartment configured to receive aggregate, a subsequent grading screen has a finer mesh size and a larger surface area than the innermost grading screen, and a space between adjacent grading screens of the plurality defines a sorting compartment;

a continuous fluid pathway passing from the receiving compartment and through the plurality of grading screens, wherein fluid communication between adjacent sorting compartments is restricted to occurring through the grading screen there between;

a first end plate configured to engage a first end of the plurality of grading screens;

a second end plate configured to engage a second end of the plurality of grading screens; and a connector extending between and joining the first end plate and the second end plate, wherein the connector resides within the receiving compartment of the innermost grading screen; and an observation container configured to receive at least a portion of the liquid and fines of the aggregate which exit the grading container, wherein the observation container includes indicia for classifying fines in the aggregate and is configured to permit at least one of observing the clarity of the liquid, measuring the volume of settled particulate matter, or measuring the turbidity of the liquid.

* * * * *